(12) United States Patent
Aysin et al.

(10) Patent No.: US 12,287,327 B2
(45) Date of Patent: Apr. 29, 2025

(54) METHOD OF DETERMINING A CONCENTRATION OF AN ANALYTE IN A BODILY FLUID

(71) Applicant: Roche Diabetes Care, Inc., Indianapolis, IN (US)

(72) Inventors: Benhur Aysin, Indianapolis, IN (US); Max Berg, Mannheim (DE); Siva Chittajallu, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 403 days.

(21) Appl. No.: 17/752,597

(22) Filed: May 24, 2022

(65) Prior Publication Data

US 2022/0283148 A1 Sep. 8, 2022

Related U.S. Application Data

(63) Continuation of application No. PCT/EP2020/083086, filed on Nov. 23, 2020.
(Continued)

(30) Foreign Application Priority Data

Jan. 22, 2020 (EP) .................................. 20153174

(51) Int. Cl.
  *G01N 33/52* (2006.01)
  *G06T 7/00* (2017.01)
  *G06T 7/90* (2017.01)

(52) U.S. Cl.
  CPC ......... *G01N 33/521* (2013.01); *G06T 7/0014* (2013.01); *G06T 7/90* (2017.01);
(Continued)

(58) Field of Classification Search
  CPC .. G01N 33/521; G01N 33/52; G01N 21/8483; G01N 21/251; G01N 21/78;
(Continued)

(56) References Cited

U.S. PATENT DOCUMENTS

| 6,122,042 A | 9/2000 | Wunderman et al. |
| 7,313,141 B2 * | 12/2007 | Kan ........................ H04L 43/00 |
| | | 370/474 |

(Continued)

FOREIGN PATENT DOCUMENTS

| EP | 0 612 035 A1 | 8/1994 |
| EP | 1 051 687 B1 | 5/2003 |

(Continued)

OTHER PUBLICATIONS

International Search Report and Written Opinion of the International Searching Authority, PCT/EP2020/083086, Mar. 26, 2021, 8 pages.
(Continued)

*Primary Examiner* — Santiago Garcia
(74) *Attorney, Agent, or Firm* — Bose McKinney & Evans LLP

(57) ABSTRACT

A method is disclosed for determining concentration of an analyte in a body fluid with a mobile device having a camera. The camera captures an image of an optical test strip having a test field. The analyte concentration value is determined from color formation of the test field. Provided in the mobile device is a correlation for transforming color formation of the test field into analyte concentration. Also provided in the mobile device is an item of clearance information indicating a level of confidence for the correlation. When the item of clearance information indicates a sufficient level of confidence for the correlation, the mobile device indicates to a user that the capturing of the image (Continued)

does not require using a color reference card. Further disclosed are a method of controlling analytical measurements, a mobile device, a system for controlling analytical measurements and computer programs for performing and/or controlling analytical measurements.

14 Claims, 5 Drawing Sheets

Related U.S. Application Data

(60) Provisional application No. 62/939,771, filed on Nov. 25, 2019.

(52) U.S. Cl.
CPC ............ *G06T 2207/10024* (2013.01); *G06T 2207/20084* (2013.01); *G06T 2207/30004* (2013.01)

(58) Field of Classification Search
CPC .... G01N 2021/1776; G01N 2201/1296; G06T 7/0014; G06T 7/90; G06T 2207/10024; G06T 2207/20084; G06T 2207/30004
See application file for complete search history.

(56) References Cited

U.S. PATENT DOCUMENTS

| | | | | |
|---|---|---|---|---|
| 8,236,516 B2* | 8/2012 | Evelegh | ............. | G01N 33/5005 435/11 |
| 9,857,373 B1* | 1/2018 | Pulitzer | .................. | G06V 10/56 |
| 10,267,813 B1* | 4/2019 | Bhatia | .................... | G01N 21/90 |
| 10,277,877 B2 | 4/2019 | Peterson et al. | | |
| 10,527,635 B1* | 1/2020 | Bhatia | .................... | G01N 35/04 |
| 10,545,163 B1* | 1/2020 | Kowalchuk | ............. | G01N 21/27 |
| 10,816,538 B2* | 10/2020 | Kluckner | ............. | G01N 33/491 |
| 11,022,620 B2* | 6/2021 | Kluckner | ............... | G01N 21/25 |
| 11,386,291 B2* | 7/2022 | Kluckner | .......... | G06F 18/24133 |
| 2005/0003468 A1* | 1/2005 | Evelegh | ................. | G01N 33/52 435/7.92 |
| 2010/0167264 A1* | 7/2010 | Lee | ......... | G01N 21/78 436/514 |
| 2011/0223673 A1* | 9/2011 | Profitt | ................ | G01N 21/8483 436/164 |
| 2012/0028245 A1* | 2/2012 | Lee | ......... | G01N 33/78 435/7.1 |
| 2013/0137121 A1* | 5/2013 | Wang | ..................... | G01N 21/17 435/7.92 |
| 2013/0267032 A1* | 10/2013 | Tsai | ......................... | G06F 18/22 436/95 |
| 2016/0080548 A1 | 3/2016 | Erickson et al. | | |
| 2022/0270720 A1* | 8/2022 | Aysin | ..................... | G16H 10/40 |

FOREIGN PATENT DOCUMENTS

| | | |
|---|---|---|
| EP | 2 916 117 A1 | 9/2015 |
| EP | 3 477 270 A1 | 5/2019 |
| EP | 3 825 691 A1 | 5/2021 |
| TW | 202132762 A | 9/2021 |
| WO | WO 99/53288 A2 | 10/1999 |
| WO | WO 2012/131386 A1 | 10/2012 |
| WO | WO 2015/007153 A2 | 1/2015 |
| WO | WO 2017/065735 A1 | 4/2017 |
| WO | WO 2018/141429 A1 | 8/2018 |
| WO | WO 2018/224442 A1 | 12/2018 |
| WO | WO 2019/081460 A1 | 5/2019 |

OTHER PUBLICATIONS

Hones et al., The Technology Behind Glucose Meters: Test Strips, Diabetes Technology & Therapeutics, vol. 10, Supplement 1, 2008, pp. S-10-S-26.

* cited by examiner

METHOD OF DETERMINING A CONCENTRATION OF AN ANALYTE IN A BODILY FLUID

RELATED APPLICATIONS

This application is a continuation of PCT/EP2020/083086, filed Nov. 23, 2020, which claims priority to EP 20 153 174.6, filed Jan. 22, 2020, and also claims priority to U.S. Patent Application No. 62/939,771, filed Nov. 25, 2019, the entire disclosures of all of which are hereby incorporated herein by reference.

BACKGROUND

This disclosure teaches a method of determining a concentration of an analyte in a bodily fluid. This disclosure further relates to a method of controlling analytical measurements using at least one mobile device having a camera. Further, this disclosure relates to a mobile device having at least one camera, to a system for controlling analytical measurements, to computer programs and computer-readable storage media. The methods, mobile devices, computer programs and storage media specifically may be used in medical diagnostics, in order to, for example, qualitatively or quantitatively detect one or more analytes in one or more body fluids, such as for detecting glucose in blood and/or interstitial fluid. Other fields of application of this disclosure, however, are feasible.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary. Without narrowing the scope, this disclosure specifically may be described with respect to blood glucose measurements. It shall be noted, however, that this disclosure may also be used for other types of analytical measurements using test elements.

Generally, devices and methods known to the skilled person make use of test elements comprising one or more test chemicals, which, in presence of the analyte to be detected, are capable of performing one or more detectable detection reactions, such as optically detectable detection reactions. With regard to the test chemicals comprised in test elements, reference may be made, e.g., to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing this disclosure.

In analytical measurements, specifically analytical measurements based on color formation reactions, one technical challenge resides in the evaluation of the color change which is due to the detection reaction. Besides using dedicated analytical devices, such as handheld blood glucose meters, the use of generally available electronics such as smart phones and portable computers or other mobile devices has become more and more popular over the recent years. As an example, WO 2012/131386 A1 discloses a testing apparatus for performing an assay, the testing apparatus comprising: a receptacle containing a reagent, the reagent being reactive to an applied test sample by developing a color or pattern variation; a portable device, e.g., a mobile phone or a laptop, comprising a processor and an image capture device, wherein the processor is configured to process data captured by the image capture device and output a test result for the applied test sample.

EP 3 477 270 A1 describes as method for evaluating the suitability of a mobile device having at least one camera for the purpose of performing an analytical measurement based on a color formation reaction. The method comprises: a) providing the at least one mobile device having at least one camera; b) providing at least one object having at least one reference color field; c) taking at least one image of at least one part of the reference color field by using the camera; and d) deriving at least one item of color resolution information by using the image.

As opposed to laboratory measurements and measurements performed by using dedicated analytical measurement devices, when using mobile computing devices such as smart phones, various influences need to be taken into account. As an example, lighting conditions, positioning, vibrations or other more or less uncontrollable conditions are to be considered.

Generally, for optical evaluation and, specifically, for the evaluation of images, a plurality of methods has been developed. Inter alia, methods using artificial neural networks (ANN) are known.

U.S. Pat. No. 6,122,042 A discloses an apparatus for photometric analysis and/or identification of properties of a material object. The apparatus comprises a collection of light sources having substantially distinct wavelength envelopes and activated in a rapid sequence of distinct combinations. The apparatus further comprises a collection of spatially distributed light detectors which detect radiation from the object and produce detected signals. A signal processor for controlling the light sources and analyzing the detected signals synchronizes the detected signals with the activation of the sequence of distinct combinations of the light sources to produce associated combinations of detected signals which are then analyzed to determine a physical property of the object and/or compared for similarity to previously detected signals from known objects. The photometric data may be combined and correlated with other measured data to enhance identification.

EP 1051687 B1 discloses systems and methods for medical diagnosis or risk assessment for a patient. These systems and methods are designed to be employed at the point of care, such as in emergency rooms and operating rooms, or in any situation in which a rapid and accurate result is desired. The systems and methods process patient data, particularly data from point of care diagnostic tests or assays, including immunoassays, electrocardiograms, X-rays and other such tests, and provide an indication of a medical condition or risk or absence thereof. The systems include an instrument for reading or evaluating the test data and software for converting the data into diagnostic or risk assessment information.

U.S. Pat. No. 10,277,877 B2 discloses a method for conversion of a series of two-dimensional images into a series of three-dimensional images. The method comprises receiving said series of two-dimensional images and, further, comprises converting said series of two-dimensional images to said series of three-dimensional images. Said converting may be based upon a neural network to determine a respective depth map associated with each of said series of two-dimensional images and processing said depth map to render said two-dimensional images as said series of three-dimensional images for being displayed on a 3D display.

EP 612035 A1 discloses a method for verification of signatures and handwriting based on comparison of extracted features, preferably using a specialized neural net.

WO 2018/224442 A1 discloses a method and an apparatus for analyzing an image using a deep neural net pre-trained for multiple classes. The image is processed by means of a forward pass through an adapted neural net to generate a processing result. The adapted neural net is adapted from the pre-trained neural net to focus on exactly one selected class. The processing result is then analyzed and focused on features corresponding to the selected class using an image processing algorithm. A modified image is generated by removing a manifestation of these features from the image.

WO 2018/141429 A1 discloses a method and an apparatus for detecting objects of interest in images. The method comprises the steps of supplying at least one input image to a trained deep neural network, which comprises a stack of layers. The method further comprises using at least one deconvolved output of at least one learned filter or combining deconvolved outputs of learned filters of at least one layer of the trained deep neural network, to detect the objects of interest in the supplied images.

WO 1999/053288 A2 discloses the use of automated systems and methods for the interpretation of Lyme Western Blots. The programs can analyze the band patterns produced by immunoblot tests, such as the Western Blot test, by scanning the test membrane by a digital camera and interpreting the test result as positive or negative. In one embodiment, a statistical analysis of band data is employed and in the other a neural network is employed. The statistical program can incorporate interpretive algorithms, such as those supported by CDC/ASTPHLD for Lyme Western Blots. The neural network is capable of learning and improving its performance, and will develop its own criteria for interpretation through the analysis of large numbers of positive and negative samples.

Despite the advantages involved in using mobile computing devices for the purpose of performing an analytical measurement, several technical challenges remain. Thus, even though artificial neural networks are generally known for image analysis, the application to the mobile-based evaluation of optical test strips, such as colorimetric test strips, remains challenging. Specifically, due to the vast amount of combined influencing factors and the ongoing release of new smartphones using new technologies, it is generally challenging to generate the required training data for the artificial neural networks in dedicated studies. Thus, in principle, for each release of a mobile device a new training study would have to be initiated which, generally, involves an immense amount of effort.

SUMMARY

This disclosure teaches devices and methods which at least partially address the above-mentioned challenges. Specifically, this disclosure teaches devices and methods which allow for a user-friendly mobile-based determination of a concentration of an analyte in a bodily fluid, with high accuracy and reproducibility, however, with low effort for setup and preparation.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "camera," "image," "test strip," and "test field," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a method of determining a concentration of an analyte in a bodily fluid is disclosed, the method comprising using a mobile device having a camera. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. The method comprises capturing at least one image of at least a part of an optical test strip having a test field, wherein the capturing comprises using the camera of the mobile device. The method further comprises determining at least one analyte concentration value from color formation of the test field.

The method further comprises:
  i) providing, in the mobile device, at least one correlation for transforming color formation of the test field into the analyte concentration value;

ii) providing, in the mobile device, at least one item of clearance information, the at least one item of clearance information indicating a level of confidence for the correlation; and iii) if the item of clearance information indicates a sufficient level of confidence for the correlation, providing, by the mobile device, indication to a user that the capturing of the at least one image does not require using the color reference card.

The term "determining the concentration of an analyte in a bodily fluid," also referred to as an "analytical measurement," as used herein, is a broad term and is to be given its ordinary and customary meaning to a person of ordinary skill in the art and is not to be limited to a special or customized meaning. The term specifically may refer, without limitation, to a quantitatively and/or qualitatively determination of at least one analyte in an arbitrary sample or aliquot of bodily fluid. For example, the bodily fluid may comprise one or more of blood, interstitial fluid, urine, saliva or other types of body fluids. The result of the determining of the concentration, as an example, may be a concentration of the analyte and/or the presence or absence of the analyte to be determined. Specifically, as an example, the analytical measurement may be a blood glucose measurement, thus the result of the analytical measurement may for example be a blood glucose concentration. In particular, an analytical measurement result value may be determined by the analytical measurement.

Consequently, the term "analyte concentration value," often also referred to as "analytical measurement result value," as used herein, is a broad term and is to be given its ordinary and customary meaning to a person of ordinary skill in the art and is not to be limited to a special or customized meaning. The term specifically may refer, without limitation, to a numerical indication of an analyte concentration in a sample.

The at least one analyte, as an example, may be or may comprise one or more specific chemical compounds and/or other parameters. As an example, one or more analytes may be determined which take part in metabolism, such as blood glucose. Additionally or alternatively, other types of analytes or parameters may be determined, e.g., a pH value.

The method, as outlined above, comprises using at least one mobile device having at least one camera. The term "mobile device" as used herein is a broad term and is to be given its ordinary and customary meaning to a person of ordinary skill in the art and is not to be limited to a special or customized meaning. The term specifically may refer, without limitation, to a mobile electronics device, more specifically to a mobile communication device such as a cell phone or smartphone. Additionally or alternatively, as will be outlined in further detail below, the mobile device may also refer to a tablet computer or another type of portable computer having at least one camera.

The term "camera" as used herein is a broad term and is to be given its ordinary and customary meaning to a person of ordinary skill in the art and is not to be limited to a special or customized meaning. The term specifically may refer, without limitation, to a device having at least one imaging element configured for recording or capturing spatially resolved one-dimensional, two-dimensional or even three-dimensional optical data or information. As an example, the camera may comprise at least one camera chip, such as at least one CCD chip and/or at least one CMOS chip configured for recording images. As used herein, without limitation, the term "image" specifically may relate to data recorded by using a camera, such as a plurality of electronic readings from the imaging device, such as the pixels of the camera chip.

The camera, besides the at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually. This disclosure specifically shall be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible.

The camera specifically may be a color camera. Thus, such as for each pixel, color information may be provided or generated, such as color values for three colors R, G, B. a larger number of color values is also feasible, such as four color values for each pixel, for example R, G, G, B. Color cameras are generally known to the skilled person. Thus, as an example, the camera chip may consist of a plurality of three or more different color sensors each, such as color recording pixels like one pixel for red (R), one pixel for green (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as R, G, G, B. The color sensitivities of the pixels may be generated by color filters or by appropriate intrinsic sensitivities of the sensor elements used in the camera pixels. These techniques are generally known to the skilled person.

The method further comprises using at least one optical test strip having at least one test field. The term "optical test strip" as used herein is a broad term and is to be given its ordinary and customary meaning to a person of ordinary skill in the art and is not to be limited to a special or customized meaning. The term specifically may refer, without limitation, to an arbitrary element or device configured for performing a color-change detection reaction. The optical test strip may also be referred to as test strip or test element, wherein all three terms may refer to the same element. The optical test strip may particularly have a test field containing at least one test chemical for detecting at least one analyte. The optical test strip, as an example, may comprise at least one substrate, such as at least one carrier, with the at least one test field applied thereto or integrated therein. In particular, the optical test strip may further comprise at least one white area, such as a white field, specifically in a proximity to the test field, for example enclosing or surrounding the test field. The white area may be a separate field independently arranged on the substrate or carrier. However, additionally or alternatively, the substrate or carrier itself may be or may comprise the white area. As an example, the at least one carrier may be strip-shaped, thereby rendering the test element a test strip. These test strips are generally widely in use and available. One test strip may carry a single test field or a plurality of test fields having identical or different test chemicals comprised therein.

As further used herein, the term "test field" is a broad term and is to be given its ordinary and customary meaning to a person of ordinary skill in the art and is not to be limited to a special or customized meaning. The term specifically may refer, without limitation, to a coherent amount of the test chemical, such as to a field, e.g., a field of round, polygonal or rectangular shape, having one or more layers of material, with at least one layer of the test field having the test chemical comprised therein.

As further outlined above, the method comprises capturing at least one image of at least a part of the at least one optical test strip having the at least one test field, by using the camera. The term "capturing at least one image" as used herein is a broad term and is to be given its ordinary and customary meaning to a person of ordinary skill in the art and is not to be limited to a special or customized meaning. The term specifically may refer, without limitation, to one or more of imaging, image recording, image acquisition, image capturing. The term "capturing at least one image" may comprise capturing a single image and/or a plurality of images such as a sequence of images. For example, the capturing of the image may comprise recording continuously a sequence of images such as a video or a movie. The capturing of the at least one image may be initiated by the user action or may automatically be initiated, e.g., once the presence of the at least one object within a field of view and/or within a predetermined sector of the field of view of the camera is automatically detected. These automatic image acquisition techniques are known, e.g., in the field of automatic barcode readers, such as from automatic barcode reading apps. The capturing of the images may take place, as an example, by acquiring a stream or "life stream" of images with the camera, wherein one or more of the images, automatically or by user interaction such as pushing a button, are stored and used as the at least one first image or the at least one second image, respectively. The image acquisition may be supported by a processor of the mobile device, and the storing of the images may take place in a data storage device of the mobile device.

The at least one image of the at least one part of the optical test strip specifically may comprise an image of at least a part of the test field. Further, the image may comprise an image of other parts of the optical test strip, such as a white reference part of the test strip.

The capturing of the at least one image may comprise capturing at least one image with having the sample of the bodily fluid applied to the test strip and, further and optionally, such as before capturing the image with the sample applied to the test strip, capturing at least one image without having the sample of the body fluid applied to the test strip. The latter image specifically may be used for comparative purposes and may also be referred to as a "blank image" or "dry image." The sample application generally may take place, as an example, directly or indirectly, e.g., via at least one capillary element. The at least one image captured after sample application may typically also be referred to as the "wet image," even though the sample may have dried when the image is actually captured. The wet image typically may be taken after having waited for at least a predetermined waiting time, such as after five seconds or more, in order to allow for the detection reaction to take place. Thus, as an example, the method may comprise, between taking the at least one optional dry image and the at least one wet image, waiting for at least a predetermined minimum amount of time. This predetermined minimum amount of time specifically may be sufficient for a detection reaction to take place in the test strip. As an example, the minimum amount of waiting time may be at least 5 s.

The method comprises determining the analyte concentration value from color formation of the test field. Thus, the method may be an analytical measurement including a change of at least one optical property of an optical test strip, which change may be measured or determined visually by using the camera. Specifically, the analytical measurement may be or may comprise a color formation reaction in the presence of the at least one analyte to be determined. The term "color formation reaction" as used herein is a broad term and is to be given its ordinary and customary meaning to a person of ordinary skill in the art and is not to be limited to a special or customized meaning. The term specifically may refer, without limitation, to a chemical, biological or physical reaction during which a color, specifically a reflectance, of at least one element involved in the reaction, changes with the progress of the reaction. The color formation may be detected by the mobile device, such as by a processor of the mobile device, and may be evaluated quantitatively, such as by deriving, from the at least one image, at least one parameter quantifying or characterizing the color formation of the test field due to the presence of the analyte in the bodily fluid. As an example, one or more of the above-mentioned color coordinates may be used. Thus, the mobile device and specifically the processor of the mobile device may be configured for determining a color change by determining a change of one or more color coordinates taking place due to the detection reaction.

The at least one analyte concentration value is determined from the color formation of the test field. For this purpose, the at least one image may be used. The analyte concentration value, as an example, may be a numerical value indicator of a result of the analytical measurement, such as indicative of the concentration of at least one analyte in the sample, such as a blood glucose concentration.

As further outlined above, in step i), the method comprises providing, in the mobile device, at least one correlation for transforming color formation of the test field into the analyte concentration value. The correlation, as an example, may be provided in an electronic format, such as in a data storage and/or via at least one interface of the mobile device. The correlation, as an example and as will be outlined in further detail below, specifically may be provided in various ways, such as by providing one or more parameters defining the correlation, such as parameters defining a linear relationship between the analyte concentration value and at least one item of information derived from the at least one image. Other types of correlation are possible.

Thus, as used herein, the term "correlation" as used herein is a broad term and is to be given its ordinary and customary meaning to a person of ordinary skill in the art and is not to be limited to a special or customized meaning. The term specifically may refer, without limitation, to a predetermined or determinable relationship between information derived from the at least one image, such as color information or color change information, and the at least one analytical measurement concentration value. For determining the analytical measurement result value from the at least one image, as an example, the correlation or predetermined or determinable relationship between information derived from the at least one image, such as color information or color change information, and the at least one analytical measurement result value may be used. This correlation or predetermined or determinable relationship, as an example, may be stored in a data storage device of the mobile device and/or in the processor of the mobile device. The processor, as an example, may be configured by software programming to derive at least one item of information from the at least one image, such as at least one color coordinate, and to apply the predetermined or determinable relationship to the at least one item of information. The correlation, as an example a transformation function, a transformation table or a lookup table, may be determined, e.g., empirically and may, as an example, be stored in at least one data storage device of the mobile device, e.g., by the software, specifically by the app downloaded from an app store or the like. As an example for deriving the at least one item of information, the processor may be programmed in order to recognize, preferably automatically, e.g., by pattern recognition and/or other algorithms, the test field or the at least one part of the test field in the images. Thereof, the processor may be programmed for determining the at least one item of information, such as one or more color coordinates. The respective at least one item of information derived from the at least one optional blank or dry image may be used for normalizing, such as by dividing the at least one item of information derived from the wet image by the at least one item of information derived from the corresponding blank image or by subtracting the at least one item of information derived from the wet image from the at least one item of information derived from the blank image or vice versa. Other ways of normalizing are feasible. The correlation, as an example a transformation function, a transformation table or a lookup table, may be determined, e.g., empirically and may, as an example, be stored in at least one data storage device of the mobile device, e.g., by the software, specifically by the app downloaded from an app store or the like.

The correlation, as will be outlined in further detail below, generally may be determined by using empirical or semi-empirical methods, also referred to as a "training." The training, as an example, may comprise performing a plurality of measurements transforming the color formation into analyte concentration values and comparing the result with at least one known result and/or by using other means of preference, such as the at least one color reference card explained in further detail below. As an example and as will be outlined in further detail below, the training may also comprise the use of one or more artificial neural networks. As an example, a plurality of images may be used as input for one or more artificial neural networks for determining the analyte concentration value, by using reference information, such as from one or more color reference cards and/or from one or more reference measurements for feedback. Other means of training are also possible and generally known to the skilled person, such as by using regression methods such as linear regression, e.g., for determining parameters of the correlation. As a result of the training, the one or more parameters characterizing the correlation may be obtained.

The method may further comprise the step of displaying the analyte concentration value, such as on a display of the mobile device. Additionally or alternatively, the method may comprise storing the at least one analyte concentration value in at least one data storage device of the mobile device. Again additionally and alternatively, the method may further comprise transmitting the at least one analyte concentration value via at least one interface and/or via at least one data transmission network, such as to another computer, e.g., for further evaluation.

As further outlined above, step ii) comprises providing, in the mobile device, at least one item of clearance information, the at least one item of clearance information indicating a level of confidence for the correlation. The at least one item of clearance information, as an example, may be provided in an electronic format, such as in at least one data storage device and/or via at least one interface of the mobile device. The term "clearance information" as used herein is a broad term and is to be given its ordinary and customary meaning to a person of ordinary skill in the art and is not to be limited to a special or customized meaning. The term specifically may refer, without limitation, to an arbitrary item of information qualifying and/or quantifying the level of confidence for the correlation. Therein, the term "level of confidence" as used herein also is a broad term and is to be given its ordinary and customary meaning to a person of ordinary skill in the art and is not to be limited to a special or customized meaning. The term specifically may refer, without limitation, to one item of information quantifying the quality of the at least one correlation. Thus, as an example, the at least one item of information may quantify, such as statistically, the correctness of the transformation of the color formation of the test field into the analyte concentration value by using the correlation. In particular, the level of confidence may quantify the quality or correctness of the transformation of the color formation of the test field into the analyte concentration value. Specifically, the level of confidence may be configured for rating and/or evaluating, e.g., quantitatively, the quality of the correlation, such as of the transformation of the color formation of the test field into the analyte concentration value. Thus, the level of confidence may indicate how good the transformation of the color formation of the test field into the analyte concentration value is. As an example, for quantifying the correctness of the transformation, various means are generally known to the person skilled in statistics, such as a correlation coefficient, a standard deviation, an interval or a degree of uncertainty, or the like. The at least one item of clearance information indicates the level of confidence, such as by using one or more numerical values, such as one or more Boolean values and/or one or more digital values, such as "sufficient" and "insufficient" or the like. As an example and as will be outlined in further detail below, in case the at least one level of confidence is above or below a predetermined threshold, the item of clearance information may be set to a specific value. As an example, one or more confidence threshold values may be used, wherein, in case the level of confidence is above the confidence threshold value, the item of clearance information may be set to "sufficient," otherwise to "insufficient" or vice versa.

Empirically or semi-empirically, the level of confidence for the correlation may be determined by using the correlation for transforming, for a plurality of test samples, the color formation of the test field for the respective test samples into calculated analyte concentration values and comparing these calculated analyte concentration values with known analyte concentration values for the respective test samples, such as known analyte concentration values determined by reference measurements, such as laboratory measurements. By statistical methods, such as regression methods, the level of confidence may be determined, as the skilled person will recognize, and may be quantified, e.g., by determining a standard deviation or the like.

As outlined above, in step iii), in case the item of clearance information indicates a sufficient level of confidence for the correlation, the method comprises providing, by the mobile device, indication to a user that the capturing of the at least one image does not require using the color reference card. Thus, as an example, the mobile device, specifically the at least one processor of the mobile device, may be configured for evaluating the at least one item of clearance information, such as by evaluating whether the item of clearance information indicates a sufficient or insufficient level of confidence for the correlation. In case the at least one item of clearance information indicates a sufficient level of confidence for the correlation, an indication is provided to the user that the capturing of the at least one image does not require using the color reference card. Thus, as an example, by default, the user may be required to use the color reference card. However, as an example, in case the at least one item of clearance information indicates an insufficient level of confidence for the correlation, the method may simply proceed, without providing indication to the user that the capturing of the at least one image does not require capturing of at least one image of at least one color reference card. Otherwise, as outlined above, indication may be provided to the user that the capturing of the at least one image does not require capturing of at least one image of the at least one color reference card.

As used herein, the term "color reference card" as used herein is a broad term and is to be given its ordinary and customary meaning to a person of ordinary skill in the art and is not to be limited to a special or customized meaning. The term specifically may refer, without limitation, to an arbitrary item having, disposed therein or disposed thereon, such as on at least one surface, at least one color reference field having known color properties or optical properties, such as having one or more colored fields having known color coordinates. As an example, the color reference card may be a flat card comprising at least one substrate having, on at least one surface and/or disposed therein, at least one color reference field having known color coordinates. Alternatively, however, the color reference card may also fully or partially be integrated into the optical test strip. The at least one image of the at least one color reference card may fully or partially be comprised by the above-mentioned image of the at least one part of the optical test strip having the test field. Thus, as an example, when capturing the at least one image of the test field, the at least one color reference card may be in the field of view of the camera and, thus, at least a part of the color reference card may be visible in the at least one image of the at least one part of the test field. As an example, the optical test strip may be placed on top of the color reference card, and/or the color reference card may comprise one or more windows, wherein the color reference card, with the one or more windows, is placed on top of the optical test strip such that the test field is visible through the window. Alternatively, however, it is also possible to capture separate images of the at least one test field and the color reference card.

The use of the color reference card specifically may allow for correcting camera specific or device specific changes in the at least one image of the color of the test field. Thus, typically, cameras and/or mobile devices, without notifying the user, apply one or more evaluation or pre-evaluation algorithms to the image, such as gamma corrections, which have to be taken into account when evaluating the images and determining the at least one analyte concentration value. By using the at least one color reference card having known optical properties, the mobile device may be set up for calibrating and/or correcting the image, thus taking into account the internal processes and/or properties of the camera and/or the mobile device when or before determining the at least one analyte concentration value. Further, ambient light influences may be taken into account. Thus, in case the at least one item of clearance information indicates that the level of confidence for the correlation is insufficient, the use of the at least one color reference card may provide additional confidence and/or correction to the method of determining the concentration, thereby increasing the accuracy and/or reliability of the analyte concentration value. Still, in case the at least one item of clearance information indicates a sufficient level of confidence, the use of the at least one color reference card, which typically requires additional handling steps and/or additional inconvenience for the user, may be obsolete and, thus, may be left out. Thereby, the method allows for increasing the accuracy if needed and in case the training of the correlation has not been finished, yet, whereas, in case the clearance information indicates a sufficient level of confidence for the correlation and, thus, indicates that the training has been finished, the transformation of the color formation of the test field into the at least one analyte concentration value may be performed without using the color reference card.

The at least one item of clearance information outlined above, may be provided in various ways. As an example, the at least one item of clearance information may be a variable which may be set, such as in a data storage device of the mobile device, and/or which may be provided to the mobile device, such as via at least one wireless or at least one wire bound interface. Thus, as an example, the at least one item of clearance information may comprise at least one clearance information flag having a state indicating an insufficient level of confidence and a state indicating a sufficient level of confidence. Thus, as an example, the at least one clearance information flag may be or may comprise a binary variable which may be set in accordance with the at least one item of clearance information and/or with respect to the sufficiency or insufficiency of the level of confidence for the correlation.

The method may further comprise:
iv) if the item of clearance information indicates an insufficient level of confidence for the correlation, providing, by the mobile device, indication to a user that the capturing of the at least one image requires capturing of at least one image of at least one color reference card.

Generally, the indication that the capturing of the at least one image does require using the color reference card and/or the indication that the capturing of the at least one image does not require using the color reference card may be provided, by the mobile device, on a display of the mobile device. Other means of indication, however, are also possible, such as audible indication or the like.

As outlined above, the at least one item of clearance information specifically may be stored in a data storage device of the mobile device. Thus, as an example, the clearance information flag may be or may comprise at least one variable, such as a binary variable, a bit, a character or the like, which is stored in the at least one data storage device of the mobile device. Similarly, the at least one correlation for transforming color formation of the test field into the analyte concentration value may be stored in a data storage device of the mobile device, such as the same data storage device used for storing the at least one item of clearance information. Thus, as an example, one or more parameters of the correlation, such as for a linear correlation an offset parameter and/or a slope parameter for transforming the at least one item of color information into the at least one analyte concentration value, may be stored in the data storage device.

The at least one correlation for transforming color formation of the test field into the analyte concentration specifically may comprise at least one of: an algorithm, a correlation matrix, a coding curve or a lookup table. Thus, as outlined above, the correlation, as an example, may comprise a coding curve such as a linear correlation coding curve, e.g., a coding curve characterized by an offset and a slope, wherein at least one item of color information derived from the image may be transformed, by the linear transformation, into the at least one analyte concentration value.

As an example, the algorithm may be based on a virtual reference device approach. Thus, as an example, a collective of several mobile devices, such as smartphones, may be used for generating a reference relative remission. Based on the reference relative remission, as an example, a slope and offset correction, such as a smartphone specific slope and offset correction, may be determined. The slope and offset correction may be used for equalizing a behavior of more than one mobile device in corrected relative remission. Based on the corrected relative remission, a common code function and/or coding curve, such as a mathematical function describing a relationship between corrective relative remission and an analyte concentration, may be determined and/or deducted.

The at least one correlation for transforming color formation of the test field into the analyte concentration may comprise a transformation of at least one item of color information derived from the at least one image into the analyte concentration. Thus, as outlined above, the mobile device may be setup, such as by software programming of the at least one processor, for deriving at least one item of color information from the at least one image, such as at least one color coordinate, such as an R, G, or B coordinate. The at least one item of color information may also indicate a change, such as by taking into account color coordinates of the dry image as compared to the wet image.

In a further aspect of this disclosure, a method of controlling analytical measurements is disclosed, the analytical measurements using at least one mobile device having a camera. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed.

The method comprises:
I) a data collection process comprising:
  a. carrying out a plurality of analytical measurements, wherein the analytical measurements, at least partly, comprise capturing images of at least a part of an optical test strip having a test field by using the camera and further comprise capturing images of at least one color reference card;
  b. evaluating the plurality of analytical measurements, thereby determining at least one correlation, the correlation being configured for transforming color formation of the test field into the analyte concentration value without requiring using the color reference card;
  c. determining a level of confidence for the correlation determined in step b.;
  d. setting at least one item of clearance information, the at least one item of clearance information indicating the level of confidence for the correlation; and
II) performing the method of determining the concentration of an analyte in a bodily fluid according to this disclosure, such as disclosed in any one of the embodiments described above and/or according to any one of the embodiments described in further detail below.

The term "method of controlling analytical measurements" as used herein is a broad term and is to be given its ordinary and customary meaning to a person of ordinary skill in the art and is not to be limited to a special or customized meaning. The term specifically may refer, without limitation, to any method which is suited for one or more of performing, optimizing, improving, initiating, triggering or handling one or more analytical measurements as defined above, wherein the at least one analytical measurement comprises using the at least one mobile device having the at least one camera.

The term "data collection process," which may also be referred to as a "training process," a "data collection period" or a "setup process," as used herein is a broad term and is to be given its ordinary and customary meaning to a person of ordinary skill in the art and is not to be limited to a special or customized meaning. The term specifically may refer, without limitation, to a process which may take place over an extended period of time, wherein during the process data is collected and used for one or more purposes of controlling, such as for one or more of improving the at least one analytical measurement or optimizing the analytical measurement. As an example and as will be outlined in further detail below, the data collection process may comprise connecting information on the analytical measurement and making use of this information for improving the level of confidence for the correlation as mentioned above.

As outlined above, the data collection process I) comprises, in step a., carrying out a plurality of analytical measurements. As defined above, an analytical measurement, also referred to as an "analyte measurement," generally may refer, without limitation, to a quantitatively and/or qualitatively determination of at least one analyte in an arbitrary sample or aliquot, specifically of bodily fluid. For further options, reference may be made to the definition given above. The analytical measurements of step a. or at least some of these analytical measurements comprise capturing images of at least a part of an optical test strip having a test field by using the camera and further comprise capturing images of at least one color reference card. Thus, the analytical measurements during the data collection process or at least some of the analytical measurements of the data collection process comprise the above-described process of using the color reference card. These analytical measurements may be used as training measurements, for the purposes of the data collection process. For details of the color reference card as well as for possible options of using the color reference card, reference may be made to the description given above. Specifically, the images of the optical test strip and the images of the color reference card may be separate images or, alternatively, at least part of the color reference card and at least part of the test field may be visible in one and the same image, thereby, e.g., forming separate sub-images of one and the same image.

As further outlined above, step b. of the data collection process comprises evaluating the plurality of analytical measurements, specifically the training measurements comprising the use of the color reference card, thereby determining at least one correlation, the correlation being configured for transforming color formation of the test field into the analyte concentration value without requiring using the color reference card. For possible solutions and embodiments of the correlation, reference may be made to the description of the method of determining an analyte given above. Further, for determining the correlation, various options are available which also, at least partially, are discussed above and which generally are known to the skilled person. Thus, generally, the images of the at least one color reference card may provide for reference data, wherein the correlation may be chosen such that a transformation of at least one item of information derived from the images of at least the part of the optical test strip having the test field into the analyte concentration by using the correlation takes into account the reference data, such as matching the reference data, thereby allowing for future analytical measurements being performed by using the correlation, without using reference data derived from the color reference card.

In the data collection process of step b., information derived from the images of the at least one color reference card may be used as reference information. Thus, as an example, from the images of the at least one color reference card, color reference information may be derived, such as for each of the analytical measurements or at least for some of the plurality of the analytical measurements of the data collection process. The color reference information derived from the images, as an example, may provide for a standardized information, wherein the color reference card, for example, has one or more known colors and wherein at least one item of color reference information may be derived from the images. Consequently, corresponding color reference information derived from the corresponding images of the test field may be compared with the color reference information derived from the images of the color reference card, which allows for correcting the changes in color which are induced by the camera and/or the mobile device. Thus, as an example, in case at least one item of color information derived from the image of the test field is equal to an item of color information derived from the image of at least one color reference field of the color reference card, and in case it is known that this color reference field corresponds to a specific analyte concentration of the analyte in the sample of the bodily fluid, a specific correlation for transforming the color formation of the test field, i.e., for transforming at least one item of color information derived from the image of the test field, into the analyte concentration value may be derived, such as a conversion factor and/or a linear correlation and/or another type of correlation, such as a mathematical relationship, which translates the item of color information of the image of the test field into the corresponding analyte concentration value. As an example, regression analysis may be used. Additionally or alternatively and as will be outlined in further detail below, artificially neuronal networks may be used. The correlation, thus, may specifically be configured for transforming at least one item of color information derived from the image of the optical test strip having the test field into the analyte concentration value. Thus, as an example, the correlation may be or may comprise one or more of a direct reference color comparison, an interpolation and an absolute color determination.

As further outlined above, in step c., a level of confidence for the correlation determined in step b. is determined. This level of confidence, as an example, may, as discussed above, be derived by using statistical analysis. Thus, as an example, from the evaluation of the training analytical measurements of step a. and their evaluation in step b., statistical analysis may be used for deriving a degree of uncertainty for the correlation. As an example, the standard deviation may be used or similar values known to the skilled person to describe a degree of uncertainty when using the correlation for transforming the at least one item of color information into the corresponding analytical concentration value, for example when using regression analysis. Similar confidence information may be derived when using artificially neuronal networks and/or any other classification method, such as decision tree, nearest neighbor or the like, for determining the correlation.

As also discussed above, in step d., at least one item of clearance information is set, the at least one item of clearance information indicating the level of confidence for the correlation derived in step b. As an example, the at least one item of clearance information simply may indicate whether the level of confidence indicates a sufficient confidence or an insufficient confidence, wherein, as discussed above in the context of the method of determining the concentration of the analyte in the bodily fluid, the method of determining the concentration of the analyte may be performed without using the color reference card once a sufficient level of confidence has been reached. As an example and as will be outlined in further detail below, the at least one item of clearance information may be set in accordance with a step function, wherein, once the at least one item of clearance information reaches at least one threshold value, the step function changes from a level indicating an insufficient level of confidence to a level indicating a sufficient level of confidence or vice versa.

As further discussed above, the method of controlling analytical measurements, besides the data collection process and/or training process in step I), also comprises, in step II), performing the method of determining the concentration of the analyte in the bodily fluid in accordance with this disclosure, i.e., according to any one of the embodiments disclosed above and/or in accordance with any one of the embodiments of this method disclosed in further detail below. It shall be noted that the training process in step I) may partially be performed outside the mobile device, whereas step II) is performed by using the mobile device. Thus, as an example, specifically, one or more of steps b., c. or d. of the training process of step I) may fully or partially be performed by at least one computer or computer system separate from the mobile device. Thus, as an example, the training data may be generated by using the mobile device for performing step a., wherein the training data or data derived thereof, including, e.g., the images or at least one item of information derived from the images may be transmitted to at least one evaluating computer, e.g., wirelessly, wherein one or more or all of steps b., c. and d. are performed at least partially by the evaluating computer. The at least one item of clearance information may be transmitted back to the mobile device by the evaluating computer. Further, the correlation or information characterizing the correlation may also be transmitted from the evaluating computer back to the mobile device, such as data characterizing an offset and/or a slope of a linear correlation or the like. In parallel or alternatively, however, the training measurements may also be fully or partially evaluated by the mobile device itself, e.g., by having the mobile device fully or partially performing one or more of steps b., c. and d.

The training process of step I) may precede the active measurement process of step II), i.e., before performing step II), a plurality of training samples may be evaluated in step I). Additionally or alternatively, however, the training may be performed iteratively, with one or more iterations of step I) being performed after having performed step II) at least once. Further, steps I) and II) at least partially may make use of the same analytical measurements, i.e., the analytical measurements of step I) a. at least partially may also function as analytical measurements for the purpose of the method of determining the concentration of the analyte in step II), which allows for using "real" measurement data also for the purpose of training, as long as the measurements comprise capturing images of the at least one color reference card. As soon as the at least one item of clearance information indicates a sufficient level of confidence for the correlation, the training may be stopped or, alternatively, such as in regular or irregular intervals, still training steps may be performed, using a color reference card, such as for improving the level of confidence of the correlation and/or for checking for the level of confidence of the correlation, such as in order to avoid and/or taking account of degradation effects, electronic shifts or other changes in the setup.

The analytical measurements carried out in step a. all may be performed under the same measurement conditions or may be performed under a variety of different measurement conditions. Thus, as an example, different measurement conditions such as different lighting conditions, different sample conditions, different temperatures, different analyte concentrations or the like may be used. These different measurement conditions may help improving the correlation, such as by taking into account factors other than the concentration of the analyte in the sample of the bodily fluid, e.g., a hematocrit value, sample temperature, lighting and the like. Specifically when using artificially neuronal networks but also when using other means of evaluation and determining the correlation such as regression methods, these factors other than the concentration of the analyte in the sample of the bodily fluid may be taken into account, such that the correlation is a function or a correlation taking into account these factors.

As outlined above, in step b. the plurality of analytical measurements of step a. are evaluated. This evaluation, as outlined above, may make use of various means, such as statistical analysis or the use of artificial neural networks. Specifically, the evaluation may also search for patterns or similarities in the images, in order to take into account these patterns or similarities for generating the correlation. Thus, generally, step b. may comprise evaluating the images captured in step a., thereby identifying similarities in at least some of the images, the similarities referring to at least one of similar patterns or similar variables, set similarities relating to specific conditions of the analytical measurements. The specific conditions of the analytical measurements may comprise, as an example, at least one of: at least one specific analyte concentration; at least one specific range of analyte concentrations; at least one specific type of the mobile device, e.g., at least one specific type of mobile phone; at least one further information, such as a manufacturer, a location, e.g., a geo-location, and a date, e.g., a date of image capturing.

Correspondingly, the level of confidence may also depend on the specific conditions of the analytical measurements. Thus, the level of confidence, as an example, may take into account factors such as specific analyte concentrations or ranges of analyte concentrations and/or the specific type of mobile phone. Additionally or alternatively, however, the level of confidence may also be specific for certain lighting conditions or the like. Thus, generally, the level of confidence determined in step c. may be a specific level of confidence for at least one of the specific conditions of the analytical measurements, specifically for a specific type of the mobile phone. As an example, several levels of confidence may be determined, such as levels of confidence for different conditions of the analytical measurements. As an example, different levels of confidence may be determined for different ranges of the analyte concentration and/or different levels of confidence may be determined for different types of mobile devices. Thus, as an example, the level of confidence for one type of mobile phone may be sufficient, whereas for another type of mobile phone the level may be insufficient, indicating the need for more training.

The identifying of similarities in at least some of the images consequently may comprise identifying similarities in groups of the images. Thus, as an example, the evaluation in step b. may comprise grouping the analytical measurements and/or the images, such as in accordance with specific features and/or in accordance with other grouping criteria such as the conditions of the analytical measurements and/or grouping criteria derived from the images.

Step b. may comprise, as outlined above, using at least one artificial neural network. The term "artificial neural network" as used herein is a broad term and is to be given its ordinary and customary meaning to a person of ordinary skill in the art and is not to be limited to a special or customized meaning. The term specifically may refer, without limitation, to a computer, a computer system, a computer network or a computer program being capable of learning to perform one or more tasks by considering one or more examples, such as without being programmed with task-specific rules. Generally, the term may refer to a system being capable of implementing a deep learning process. Specifically, the at least one artificial neural network may comprise at least one self-learning or machine-learning system. As an example, the artificial neural network may comprise at least one input layer having a plurality of nodes, at least one output layer having a plurality of nodes and optionally one or more hidden layers in between the input layer and the output layer. The nodes between neighboring layers may be interconnected by signal connections. The artificial neural network specifically may simulate the learning process of the human brain. The at least one artificial neural network specifically may be or may comprise at least one convolutional neural network. As the skilled person will appreciate, an artificial neural network specifically may be used for identifying or analyzing images and/or for identifying features or similarities in a plurality of images. Consequently, as an example, the at least one artificial neural network may be used for identifying the similarities in at least some of the images. The similarities specifically may refer to at least one of: similar patterns, similar variables, similarities relating to specific conditions of the analytical measurements.

As outlined above, several means for setting the at least one item of clearance information may generally be possible, such as using comparisons with at least one threshold value and/or applying at least one step function. Thus, as an example, step d. may comprise comparing the level of confidence with at least one predetermined threshold value, specifically a predetermined minimum value, and, based on the comparison, setting the at least one item of clearance information to a value indicating an insufficient level of confidence for measurements without using the color reference card or a sufficient level of confidence for measurements without using the color reference card, respectively.

In a further aspect of this disclosure, a mobile device is disclosed, the mobile device having at least one camera, and the mobile device being configured for performing the method of determining a concentration of an analyte in a bodily fluid according to this disclosure, such as according to any one of the embodiments disclosed above and/or according to any one of the embodiments disclosed in further detail below. Specifically, the mobile device may comprise at least one processor. The term "processor" as used herein is a broad term and is to be given its ordinary and customary meaning to a person of ordinary skill in the art and is not to be limited to a special or customized meaning.

The term specifically may refer, without limitation, to an arbitrary logic circuitry configured for performing basic operations of a computer or system, and/or, generally, to a device which is configured for performing calculations or logic operations. In particular, the processor may be configured for processing basic instructions that drive the computer or system. As an example, the processor may comprise at least one arithmetic logic unit (ALU), at least one floating-point unit (FPU), such as a math coprocessor or a numeric coprocessor, a plurality of registers, specifically registers configured for supplying operands to the ALU and storing results of operations, and a memory, such as an L1 and L2 cache memory. In particular, the processor may be a multi-core processor. Specifically, the processor may be or may comprise a central processing unit (CPU). Additionally or alternatively, the processor may be or may comprise a microprocessor, thus specifically the processor's elements may be contained in one single integrated circuitry (IC) chip. Additionally or alternatively, the processor may be or may comprise one or more application-specific integrated circuits (ASICs) and/or one or more field-programmable gate arrays (FPGAs) and/or one or more tensor processing unit (TPU) and/or one or more chip, such as a dedicated machine learning optimized chip, or the like.

The processor specifically may be configured, such as by software programming, for performing and/or supporting the method steps of the method. Specifically, the processor may be configured for supporting the capturing of the at least one image of the at least one part of the optical test strip having the test field by using the camera. The processor may further be configured for determining at least one analyte concentration value from color formation of the test field, such as by evaluating the image, deriving at least one item of information from the image and by transforming the at least one item of information into the at least one analyte concentration value. The processor specifically may further be configured for supporting one or more or all of steps i), ii) and iii) of the method, such as for providing and/or receiving the correlation, such as for providing answers or receiving the at least one item of clearance information and for evaluating the at least one item of clearance information as well as for further providing the indication to the user that the capturing of the at least one image does not require using a color reference card. The processor may further be configured for supporting sample application to the test strip, such as by providing user guidance, e.g., in a visual format and stuff or in an audible format. The processor may further be configured for supporting the capturing of the at least one image, e.g., by automatically detecting the test strip or a part thereof in a field of view and/or by prompting the user to capture the image.

In a further aspect of this disclosure, a system for controlling analytical measurements is disclosed. The system comprises at least one mobile device having at least one camera. The system further is configured for carrying out the method of controlling analytical measurements using the at least one mobile device according to this disclosure, such as according to any one of the embodiments disclosed above and/or according to any one of the embodiments disclosed in further detail below. Thus, the system generally may comprise a plurality of components configured for interacting. Thus, besides the at least one mobile device, the system specifically may comprise at least one evaluation device configured for performing at least steps b., c. and d. The evaluation device, for example, may be connected to the mobile device, specifically in a wireless fashion, such as via the Internet and/or via a wireless communications network.

The evaluation device, as an example, may comprise one or more of a computer and a computer system, such as one or more of a server, a server system or a cloud-based server or server system, which is configured, by software programming, for performing at least steps b., c. and d. The evaluation device may further be configured for receiving, specifically wirelessly, results generated in step a., such as the images and/or parts thereof and/or at least one item of information derived from the images, such as at least one item of color information and/or at least one analytical measurement value derived thereof. In turn, the evaluation device may further be configured for transmitting the at least one item of clearance information to the mobile device, e.g., in a wireless fashion. For receiving and transmitting, the evaluation device may comprise at least one receiver and/or at least one transmitter.

The evaluation device specifically may be separate from the mobile device, such as remote from the mobile device. The evaluation device, as outlined above, specifically may be configured for communicating with the mobile device, specifically in a wireless fashion. The evaluation device may comprise at least one of: a server device and a cloud-based evaluation device. The evaluation device specifically may be configured for transmitting the at least one item of clearance information to the mobile device.

In further aspects of this disclosure, computer programs and computer-readable storage media are disclosed which fully or partially support or perform the methods according to this disclosure, i.e., one or both of the method of determining the concentration of an analyte and/or the method of controlling analytical measurements, e.g., in one or more of the embodiments disclosed above and/or in one or more of the embodiments disclosed in further detail below. Thus, in a further aspect, a computer program comprising instructions which, when the program is executed by a mobile device having a camera, specifically by a processor of the mobile device, cause the mobile device to carry out the method of determining the concentration of an analyte in a bodily fluid according to this disclosure, such as according to any one of the embodiments disclosed above and/or according to any one of the embodiments disclosed in further detail below. Similarly, a computer-readable storage medium comprising instructions which, when executed by a mobile device having a camera, specifically by a processor of the mobile device, cause the mobile device to carry out the method of determining the concentration of an analyte in a bodily fluid according to this disclosure, such as according to any one of the embodiments disclosed above and/or according to any one of the embodiments disclosed in further detail below. Further, a computer program is disclosed, comprising instructions which, when the program is executed by the system for controlling analytical measurements according to this disclosure, such as according to any one of the embodiments disclosed above and/or according to any one of the embodiments disclosed in further detail below, cause the system to carry out the method of controlling analytical measurements according to this disclosure, such as according to any one of the embodiments disclosed above and/or according to any one of the embodiments disclosed in further detail below. Similarly, a computer-readable storage medium is disclosed, comprising instructions which, when executed by the system for controlling analytical measurements according to this disclosure, such as according to any one of the embodiments disclosed above and/or according to any one of the embodiments disclosed in further detail below, cause the system to carry out the method of controlling analytical measurements according to this disclosure, such as according to any one of the embodiments disclosed above and/or according to any one of the embodiments disclosed in further detail below.

As used herein, the term "computer-readable storage medium" specifically may refer to a non-transitory data storage means, such as a hardware storage medium having stored thereon computer-executable instructions. The computer-readable data carrier or storage medium specifically may be or may comprise a storage medium such as a random-access memory (RAM) and/or a read-only memory (ROM).

The computer program may also be embodied as a computer program product. As used herein, a computer program product may refer to the program as a tradable product. The product may generally exist in an arbitrary format, such as in a paper format, or on a computer-readable data carrier and/or on a computer-readable storage medium. Specifically, the computer program product may be distributed over a data network.

The methods and devices according to this disclosure provide a large number of advantages over similar methods and devices known in the art. Thus, compared to methods and devices known in the art, the methods and devices as described herein may increase measurement flexibility and handling. Specifically, measurement flexibility and handling may be increased by allowing a vast number of mobile devices to be used for analyte measurement determination and controlling. The vast number of mobile devices that this disclosure may allow to be used for analytical measurements may even be a growing number of mobile devices due to ongoing releases, such as ongoing releases of new smartphones. In particular, the methods and devices according to this disclosure may allow the use of these mobile devices by performing a training process, for example generating training data. In particular, generating training data while performing the analyte measurements may be preferable to complex and time consuming dedicated studies for generating training data in a laboratory environment.

Further, the present methods and devices, e.g., by using a reference card, may increase measurement safety over known methods and devices. Specifically, using the reference card according to this disclosure, e.g., generating reference card measurement data, may be used for training an artificial neural network, such as an image based neural net. Thus, analytical measurements according to this disclosure may be safer than measurement known from the art, e.g., by allowing methods and devices to be adapted to real circumstances and conditions, such as to smartphone specific and scene specific aspects.

Moreover, measurement performance may be enhanced by the present methods and devices, due to allowing, e.g., after an initial data collection process, determining an analyte measurement concentration independent of the reference card. Thus, the reference card may no longer be required as soon as enough data may have been collected and/or the artificial network may be trained. A simplicity of no longer requiring the reference card for determining the analyte concentration, may further improve user handling.

Summarizing and without excluding further possible embodiments, the following embodiments may be envisaged:

Embodiment 1: A method of determining a concentration of an analyte in a bodily fluid, the method comprising using a mobile device having a camera, wherein the method comprises capturing at least one image of at least a part of an optical test strip having a test field by using the camera, and wherein the method further comprises determining at least one analyte concentration value from color formation of the test field, wherein the method comprises:
  i) providing, in the mobile device, at least one correlation for transforming color formation of the test field into the analyte concentration value;
  ii) providing, in the mobile device, at least one item of clearance information, the at least one item of clearance information indicating a level of confidence for the correlation; and
  iii) if the item of clearance information indicates a sufficient level of confidence for the correlation, providing, by the mobile device (112), indication to a user that the capturing of the at least one image does not require using the color reference card.

Embodiment 2: The method according to the preceding embodiment, wherein the at least one item of clearance information comprises a clearance information flag having a state indicating an insufficient level of confidence and a state indicating a sufficient level of confidence.

Embodiment 3: The method according to any one of the preceding embodiments, wherein the method further comprises:
  iv) if the item of clearance information indicates an insufficient level of confidence for the correlation, providing, by the mobile device (112), indication to a user that the capturing of the at least one image requires capturing of at least one image of at least one color reference card.

Embodiment 4: The method according to any one of the preceding embodiments, wherein the indication is provided, by the mobile device, on a display of the mobile device.

Embodiment 5: The method according to any one of the preceding embodiments, wherein the at least one item of clearance information is stored in a data storage device of the mobile device.

Embodiment 6: The method according to any one of the preceding embodiments, wherein the at least one correlation for transforming color formation of the test field into the analyte concentration value is stored in a data storage device of the mobile device.

Embodiment 7: The method according to any one of the preceding embodiments, wherein the at least one correlation for transforming color formation of the test field into the analyte concentration comprises at least one of an algorithm, a correlation matrix, a coding curve or a lookup table.

Embodiment 8: The method according to any one of the preceding claims, wherein the at least one correlation for transforming color formation of the test field into the analyte concentration comprises a transformation of at least one item of color information derived from the at least one image into the analyte concentration.

Embodiment 9: A method of controlling analytical measurements using at least one mobile device having a camera, the method comprising:
  I) a data collection process comprising:
    a. carrying out a plurality of analytical measurements, wherein the analytical measurements, at least partly, comprise capturing images of at least a part of an optical test strip having a test field by using the camera and further comprise capturing images of at least one color reference card;
    b. evaluating the plurality of analytical measurements, thereby determining at least one correlation, the correlation being configured for transforming color formation of the test field into the analyte concentration value without requiring using the color reference card;

c. determining a level of confidence for the correlation determined in step b.;

d. setting at least one item of clearance information, the at least one item of clearance information indicating the level of confidence for the correlation; and II) performing the method of determining the concentration of an analyte in a bodily fluid according to any one of the preceding embodiments.

Embodiment 10: The method according to the preceding embodiment, wherein the analytical measurements carried out in step a. at least partially are carried out under a variety of different measurement conditions.

Embodiment 11: The method according to any one of the two preceding embodiments, wherein step b. comprises evaluating the images captured in step a., thereby identifying similarities in at least some of the images, the similarities specifically referring to at least one of similar patterns, similar variables, similarities relating to specific conditions of the analytical measurements.

Embodiment 12: The method according to the preceding embodiment, wherein the specific conditions of the analytical measurements comprise at least one of: at least one specific analyte concentration; at least one specific range of analyte concentrations; at least one specific type of the mobile device; at least one further information, such as a manufacturer, a location, e.g., a geo-location, and a date, e.g., a date of image capturing.

Embodiment 13: The method according to the preceding embodiment, wherein the level of confidence determined in step c. is a specific level of confidence for at least one of the specific conditions of the analytical measurements, specifically for a specific type of the mobile device.

Embodiment 14: The method according to any one of the three preceding embodiments, wherein the identifying of similarities in at least some of the images comprises identifying similarities in groups of the images.

Embodiment 15: The method according to any one of the six preceding embodiments, wherein step b. comprises using an artificial neural network, specifically for identifying the similarities in at least some of the images, the similarities referring to at least one of similar patterns or similar variables, set similarities relating to specific conditions of the analytical measurements.

Embodiment 16: The method according to any one of the seven preceding embodiments, wherein step d. comprises comparing the level of confidence with a predetermined threshold value, specifically a predetermined minimum value, and, based on the comparison, setting the at least one item of clearance information to a value indicating an insufficient level of confidence for measurements without using the color reference card or a sufficient level of confidence for measurements without using the color reference card, respectively.

Embodiment 17: A mobile device having at least one camera, the mobile device being configured for performing the method of determining a concentration of an analyte in a bodily fluid according to any one of embodiments 1 to 8.

Embodiment 18: The mobile device according to the preceding embodiment, wherein the mobile device further comprises at least one processor.

Embodiment 19: A system for controlling analytical measurements, the system comprising at least one mobile device having at least one camera, the system being configured for carrying out the method according to any one of embodiments 9 to 16.

Embodiment 20: The system according to the preceding embodiment, wherein the system comprises at least one evaluation device configured for performing at least steps b., c. and d.

Embodiment 21: The system according to the preceding embodiment, wherein the evaluation device is separate from the mobile device and is configured for communicating with the mobile device.

Embodiment 22: The system according to any one of the two preceding embodiments, wherein the evaluation device comprises at least one of a server device and a cloud-based evaluation device.

Embodiment 23: The system according to any one of the three preceding embodiments, wherein the evaluation device is configured for transmitting the at least one item of clearance information to the mobile device.

Embodiment 24: A computer program comprising instructions which, when the program is executed by a mobile device having a camera, specifically by a processor of the mobile device, cause the mobile device to carry out the method of any one of embodiments 1 to 8.

Embodiment 25: A computer-readable storage medium comprising instructions which, when executed by a mobile device having a camera, specifically by a processor of the mobile device, cause the mobile device to carry out the method of any one of the embodiments 1 to 8.

Embodiment 26: A computer program comprising instructions which, when the program is executed by the system according to any one of embodiments 19 to 23, cause the system to carry out the method of any one of embodiments 9 to 16.

Embodiment 27: A computer-readable storage medium comprising instructions which, when executed by the system according to any one of embodiments 19 to 23, cause the system to carry out the method of any one of embodiments 9 to 16.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
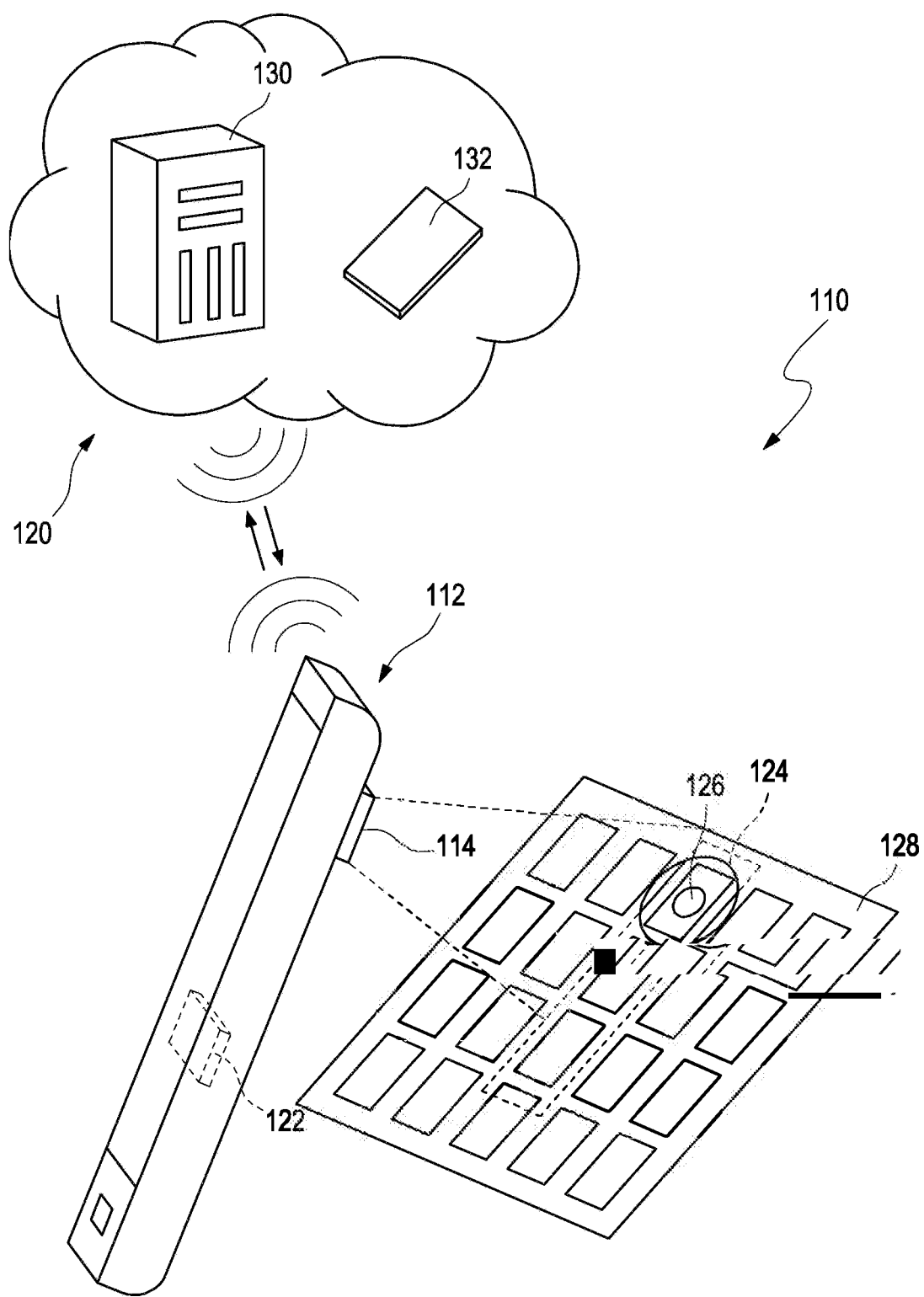
FIG. 1 shows embodiments of a system for controlling analytical measurements and a mobile device in a perspective view.
Figure 2:
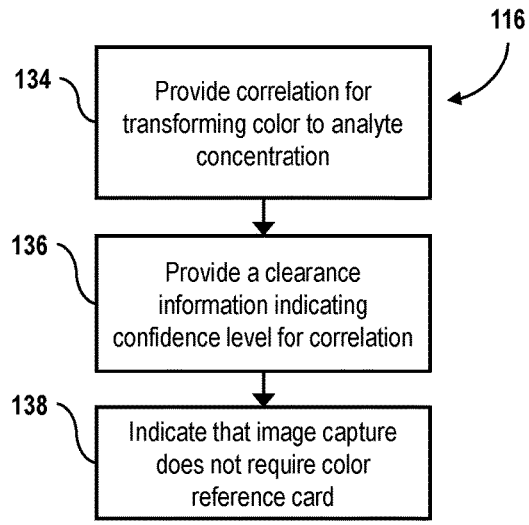
FIGS. 2 and 3 show flow charts of different embodiments of a method of determining a concentration of an analyte in a bodily fluid.

In FIG. 1 embodiments of a system 110 for controlling analytical measurements and a mobile device 112 are illustrated in a perspective view. The mobile device 112 has at least one camera 114. Further, the mobile device 112 is configured for performing a method 116 of determining a concentration of an analyte in a bodily fluid. The method 116 of determining a concentration of an analyte in a bodily fluid may also be referred to as determination method 116. The determination method 116 will be described with reference to exemplary embodiments shown in flowcharts illustrated in FIGS. 2 and 3. The system 110 comprises the at least one mobile device 112 having the at least one camera 114. The system 110 is further configured for carrying out a method 118 of controlling analytical measurements. The method 118 of controlling analytical measurements may also be referred to as controlling method 118. The controlling method 118 will be described with reference to exemplary embodiments shown in flowcharts illustrated in FIGS. 4 and 6.

The system 110 may further comprise at least one evaluation device 120. The evaluation device 120 may specifically be separate from the mobile device 112 and may be configured for communicating with the mobile device 112, illustrated in FIG. 1 by two arrows pointing in opposite directions. In particular, at least one item of clearance information may be transmitted by the evaluation device 120 to the mobile device 112. As an example, the evaluation device 120 may comprise at least one of a server device 130 and a cloud-based evaluation device 132. The mobile device may further comprise at least one processor 122. The processor 122 may specifically support an image acquisition of the mobile device 112, such as a capturing of images of at least a part of an optical test strip 124 having a test field 126. Further illustrated in FIG. 1 is a color reference card 128.

The method 116 of determining a concentration of an analyte in a bodily fluid comprises using a mobile device 112 having a camera 114. The method 116 further comprises capturing at least one image of at least a part of an optical test strip 124 having a test field 126 by using the camera 114. The method 116 further comprises determining at least one analyte concentration value from color formation of the test field 126. Furthermore, the method 116 comprises the following steps, which may specifically be performed in the given order. Still, a different order may also be possible. It may be possible to perform two or more of the method steps fully or partially simultaneously. It may further be possible to perform one, more than one or even all of the method steps once or repeatedly. The method 116 may comprise additional method steps that are not listed. The method steps of the method 116 are the following:
  i) (denoted with reference number 134) providing, in the mobile device 112, at least one correlation for transforming color formation of the test field 126 into the analyte concentration value;
  ii) (denoted with reference number 136) providing, in the mobile device 112, at least one item of clearance information, the at least one item of clearance information indicating a level of confidence for the correlation; and
  iii) (denoted with reference number 138) if the item of clearance information indicates a sufficient level of confidence for the correlation, providing, by the mobile device 112, indication to a user that the capturing of the at least one image does not require using the color reference card 128.

Figure 3:
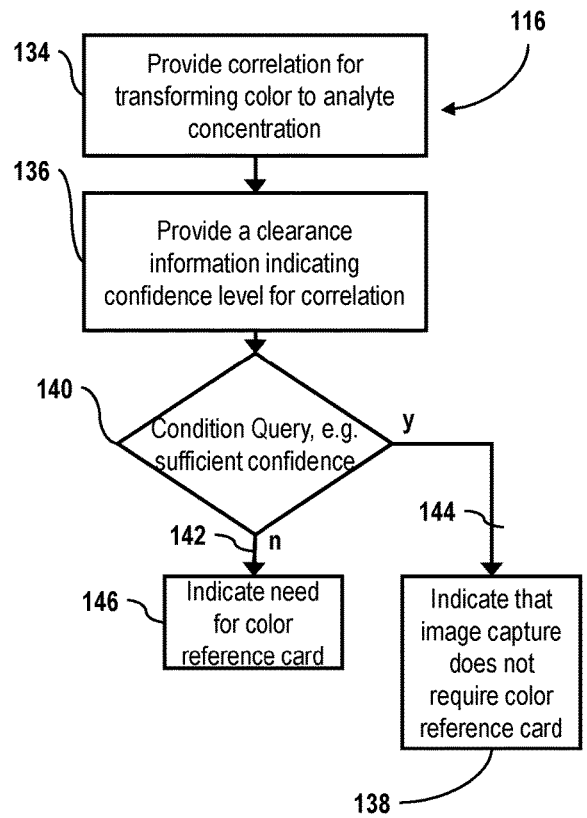
Figure 4:
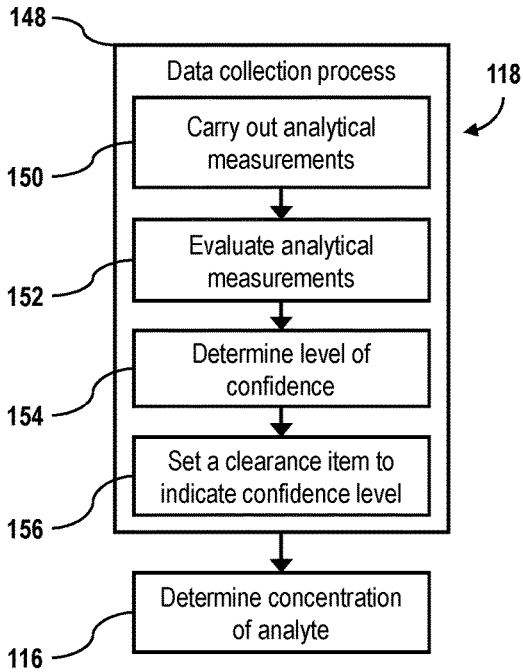
FIG. 4 shows a flow chart of an embodiment of a method of controlling analytical measurements.

Further, as exemplarily illustrated in FIG. 3, the method 116 may comprise a branching point 140. The branching point 140 may indicate a condition query, such as deciding between a first branch 142 and a second branch 144. For example, the condition query may make use of the item of clearance information. The item of clearance information may, for example, comprise a clearance information flag having a state indicating an insufficient level of confidence and a state indicating a sufficient level of confidence. Thus, the item of clearance information may comprise Boolean information, such as "sufficient" ("y") or "insufficient" ("n"). As an example, the first branch 142 may indicate an insufficient level of confidence and may lead to step iv) (denoted with reference number 146) if the item of clearance information indicates an insufficient level of confidence for the correlation, providing, by the mobile device 112, indication to a user that the capturing of the at least one image requires capturing of at least one image of at least one color reference card 128. The second branch 144 indicates a sufficient level of confidence and, thus, leads to step iii) 138.

The method 118 of controlling analytical measurements using at least one mobile device 112 having a camera 114 comprises the following steps, which may specifically be performed in the given order. Still, a different order may also be possible. It may be possible to perform two or more of the method steps fully or partially simultaneously. It may further be possible to perform one, more than one or even all of the method steps once or repeatedly. The method 118 may comprise additional method steps that are not listed. The method steps of the method 118 are the following:
  I) (denoted with reference number 148) a data collection process comprising:
    a. (denoted with reference number 150) carrying out a plurality of analytical measurements, wherein the analytical measurements, at least partly, comprise capturing images of at least a part of an optical test strip 124 having a test field 126 by using the camera 114 and further comprise capturing images of at least one color reference card 128;
    b. (denoted with reference number 152) evaluating the plurality of analytical measurements, thereby determining at least one correlation, the correlation being configured for transforming color formation of the test field 126 into the analyte concentration value without requiring using the color reference card 128;
    c. (denoted with reference number 154) determining a level of confidence for the correlation determined in step b.;
    d. (denoted with reference number 156) setting at least one item of clearance information, the at least one item of clearance information indicating the level of confidence for the correlation; and
  II) performing the method 116 of determining the concentration of an analyte in a bodily fluid.

Figure 5:
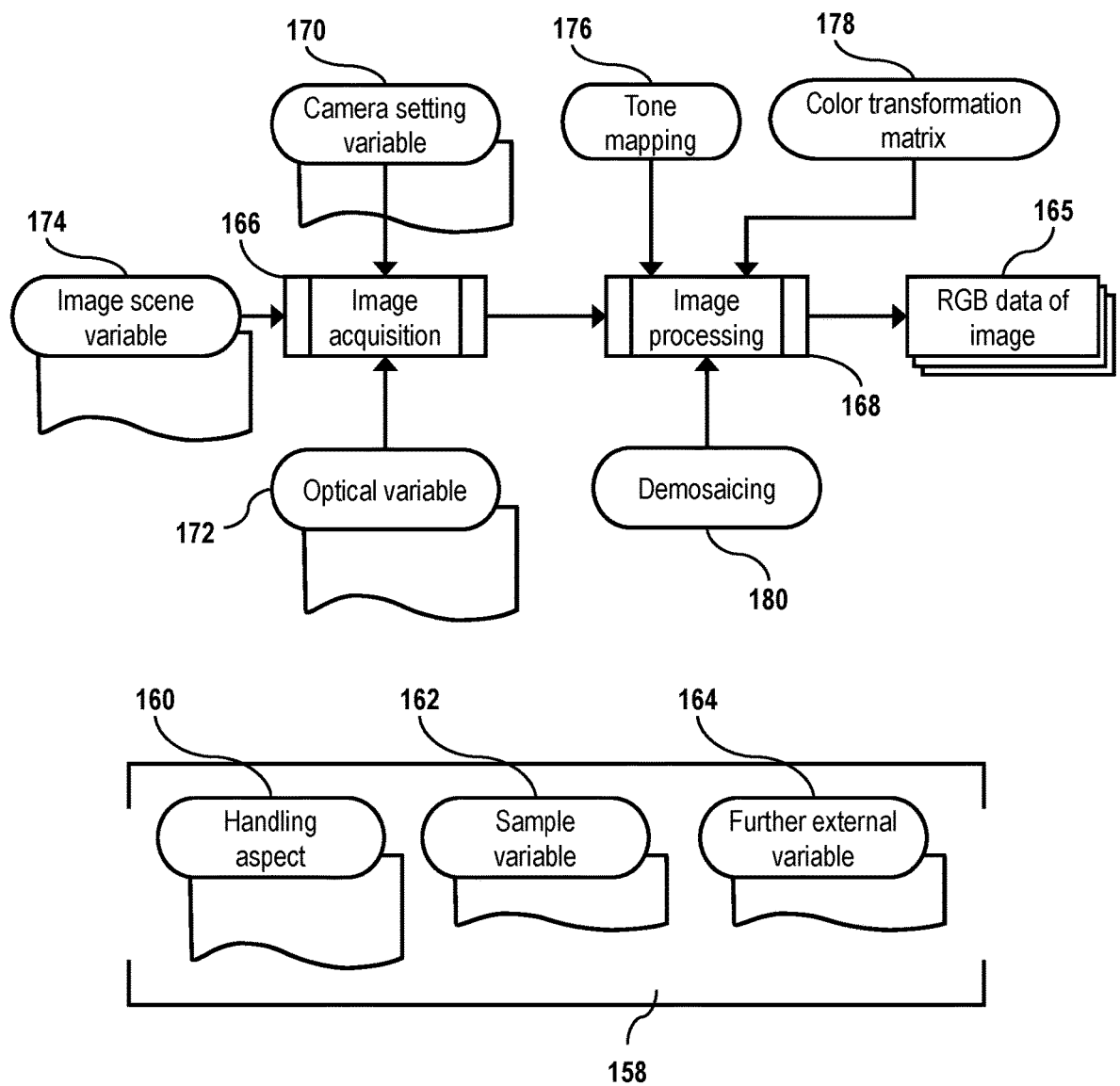
FIG. 5 shows influencing factors on a method of determining a concentration of an analyte in a bodily fluid.

In particular, step b. may comprise using an artificial neural network, specifically for identifying similarities in at least some of the images. Specifically, the similarities may refer to at least one of similar patterns or similar variables. In detail, the similarities may relate to specific conditions of the analytical measurements. The analytical measurement, specifically the method of determining a concentration of an analyte in a bodily fluid, may be subjected to various influencing factors, as exemplarily illustrated in FIG. 5. External factors 158 that may influence the analytical measurement may be or may comprise handling aspects 160, sample variables 162 and further external variables 164. As an example, handling aspects 160 may be or may comprise a temporal aspect, e.g., a timing, and an angular or spatial orientation, e.g., an angular or spatial orientation of the optical test strip 124 and the camera 114. Sample variables 162, for example, may be or may comprise characteristics of the sample influencing the analytical measurement, such as hematocrit (hct), blood volume and interferences, such as maltose or the like. Further external variables 164 may, for example, comprise temperature and humidity.

Further influencing factors may affect the analytical measurement by occurring or interfering when capturing the at least one image, for example in steps iii) 138 and a. 150. In particular, the capturing of the at least one image, for example in order to retrieve RGB data 165 of the image, may comprise at least two sub-steps, such as an image acquisition 166 and an image processing 168, which, for example, may be affected by different influencing factors. Thus, as an example, the image acquisition 166 may be influenced by properties or characteristics of the mobile device 112, e.g., of a smartphone, such as by camera setting variables 170, e.g., exposure time, ISO settings, RGGB gains or the like, and by optical variables 172 that may include sensor setting, such as aperture, focal length, reproduction scale, pixel resolution and sensor type, e.g., a Bayer sensor. Further, the image acquisition 166 may be influenced by image scene variables 174, such as ambient light, e.g., an intensity and/or a spectral distribution, a background, e.g., background lighting or color, and an optical test strip 124 to background ratio, e.g., a pixel ratio between pixels representing the optical test strip 124 and pixels representing the background. Properties or characteristics of the mobile device 112 that may influence the image processing 168 may be or may comprise tone mapping 176, color transformation matrix 178 and demosaicing 180.

Figure 6:
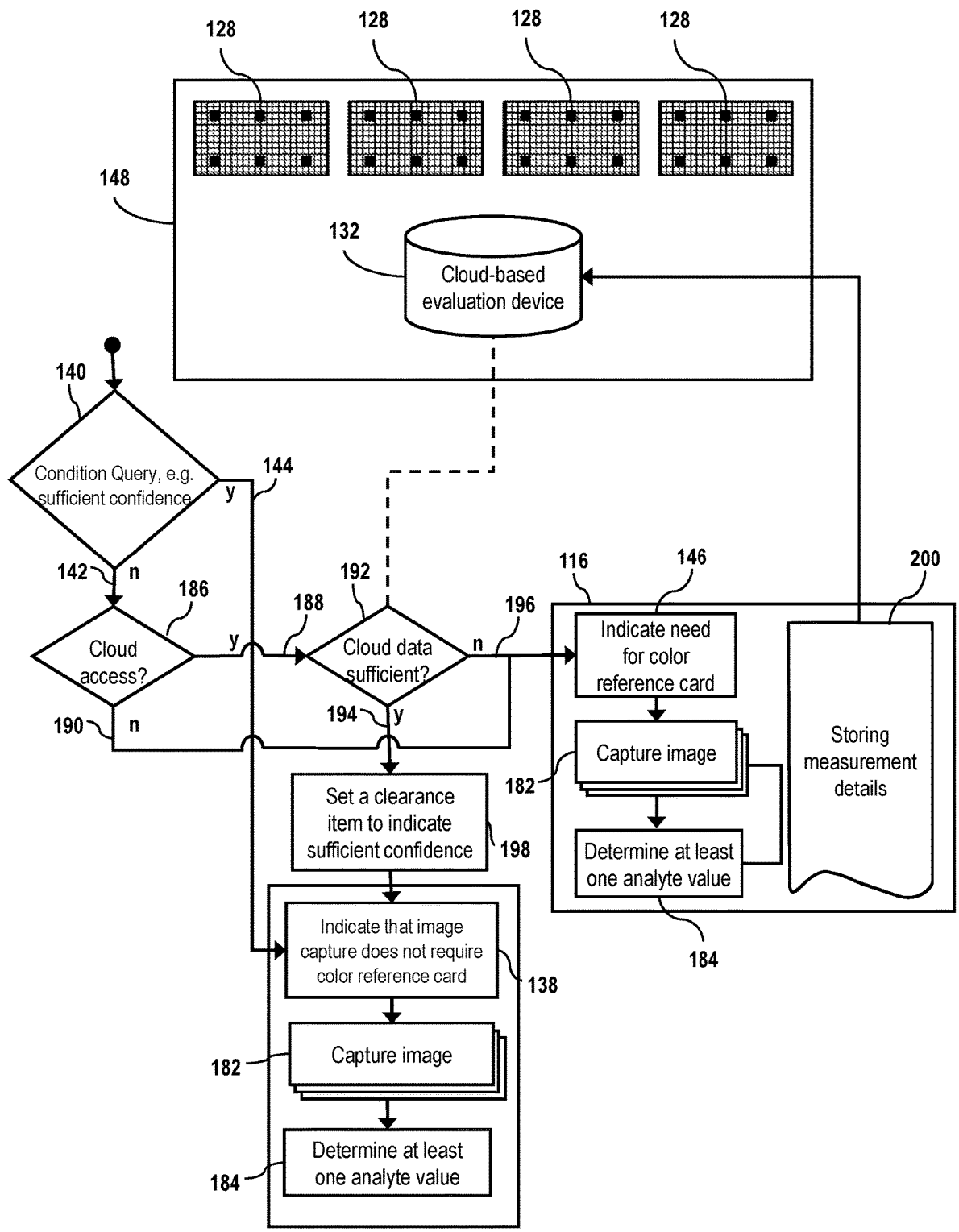
FIG. 6 shows a flow chart of an embodiment of a method of controlling analytical measurements.

In FIG. 6, a flow chart of an embodiment of a method of controlling analytical measurements is illustrated. Therein, as an example, a black point or circle in the upper left corner of the FIG. 6 illustrates a starting point of the method 118 of controlling analytical measurements. As exemplarily illustrated in FIG. 6, the method 118 may start with branching point 140 deciding between the second branch 144 that may indicate the clearance information flag having a state indicating a "sufficient" ("y") level of confidence and may lead to step iii) 138. Subsequently, a capturing 182 of at least one image of at least a part of an optical test strip 124 having a test field 126 by using the camera 114 may be performed without requiring using the color reference card 128. Step 182 may specifically be followed by determining 184 at least one analyte concentration value from color formation of the test field 126.

The first branch 142 may indicate the clearance information flag having a state indicating an "insufficient" ("n") level of confidence and may lead to a next branching point 186 deciding between a first branch 188 and a second branch 190. The first branch 142 may be the "default" branch or default setting, such that the user, by default, may be required to use the color reference card 128. The branching point 186 may comprise a check of cloud access 186, such as a determination whether the mobile device 112 may have access to data collected in the data collection process I) 148, for example stored on a cloud-based evaluation device 132, or not. Thus, the first branch 188 may indicate "cloud access" ("y") and may lead to a further branching point 192 deciding between a first branch 194 and a second branch 196 on whether the data collected in the data collection process I) 148 indicates a "sufficient" ("y") or "insufficient" ("n") level of confidence. Specifically the query 192 may comprise a strip only clearance check for the mobile device 112, such as by determining if the level of confidence determined in step c. 154 is sufficient or insufficient. As illustrated, the first branch 194 may indicate a "sufficient" ("y") level of confidence and may thus, lead to a step of setting 198 the clearance information flag to a state indicating a sufficient level of confidence and may subsequently lead to performing the method 116, specifically to step iii) 138, as described above. The second branch 190 may indicate "no cloud access." The second branch 196 may indicate the data collected in the data collection process I) 148 to indicate an "insufficient" level of confidence.

Both, the second branch 190 and the second branch 196 may lead to step iv) 146. Thus, for both cases, e.g., for the case of the mobile device 112 being considered to have "no cloud access" and for the case of the data collected in the data collection process I) 148 indicating an "insufficient" level of confidence, the outcome may be the same. Specifically, the method 116 of determining the concentration of an analyte in a bodily fluid may be performed, wherein the capturing 182 of the at least one image of at least a part of an optical test strip 124 having a test field 126 by using the camera 114 requires using the at least one reference card 128. Again, step 182 may be followed by determining 184 at least one analyte concentration value from color formation of the test field 126. In particular, the performing of method 116, wherein capturing 182 of the at least one image requires capturing of at least one image of at least one color reference card 128, may further comprise storing 200 measurement details, such as meta data, e.g., images, at least one intermediate step and at least one smartphone meta data. In detail, the at least one intermediate step may specifically be or may comprise an intensity correction, a color correction and a color reference card quality check. Further, the at least one smartphone meta data may be or may comprise information on a smartphone used for capturing the at least one image, such as a manufacturer, a model type, automatic settings, e.g., used auto setting, and hardware information. The measurement details may be used in the data collection process I) 148, specifically in step b. 152, as is exemplarily illustrated by the arrow in FIG. 6 pointing from method 116 to step I) 148. As an example, measurement details from various measurements, for example using different embodiments of color reference cards 128, may be used.

Figure 7:
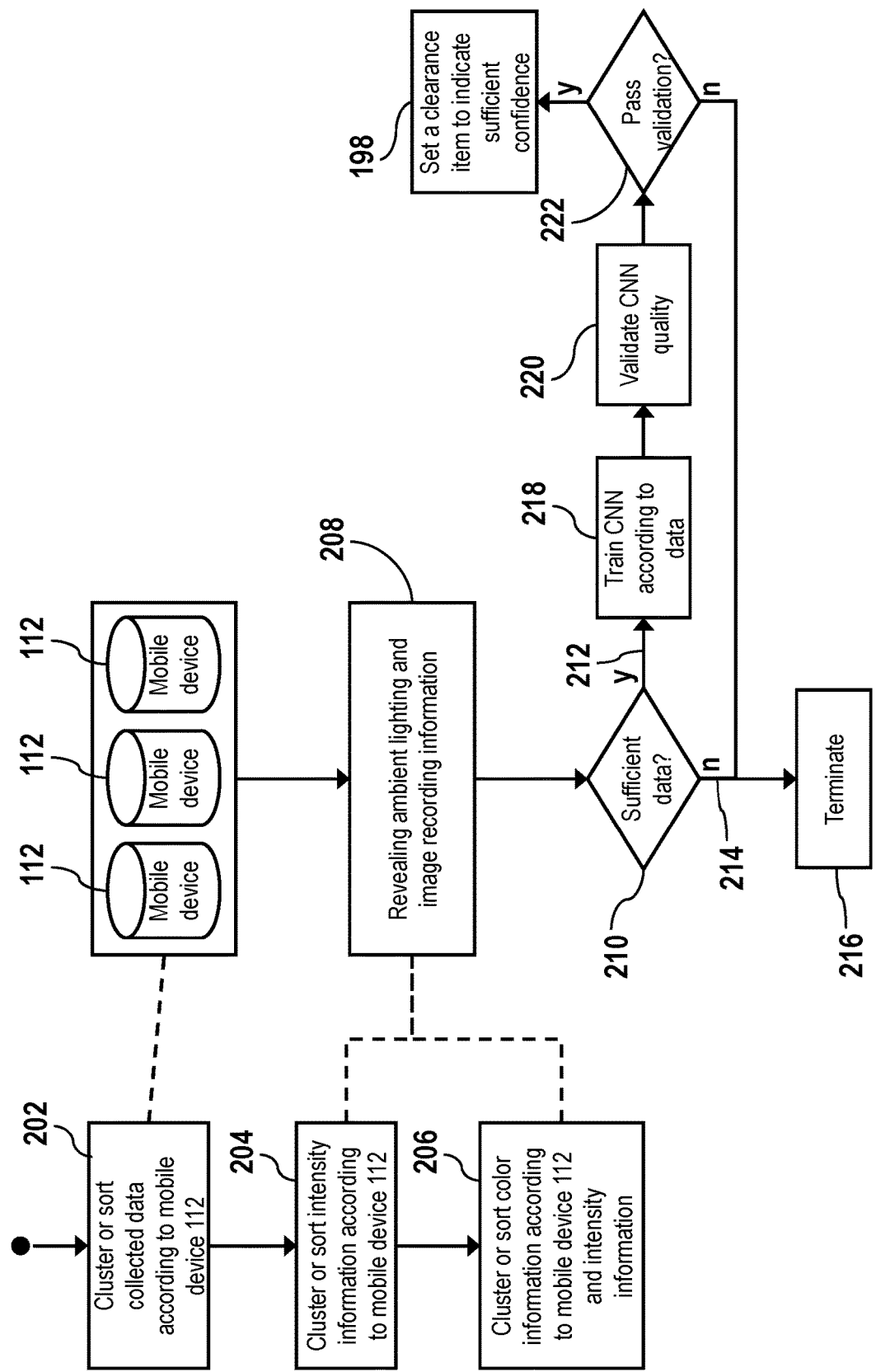
FIG. 7 shows a flow chart of a part of a method of controlling analytical measurements.

In FIG. 7, a flow chart of a part of a method 118 of controlling analytical measurements is illustrated. Specifically, details on step I) 148 are illustrated. Again, the black point or circle in the upper left corner of the FIG. 7 illustrates a starting point. Firstly, on an evaluation device 120, the collected data may be clustered or sorted (denoted with reference number 202) according to the mobile device 112 used for generating the specific collected data, such as according to phone model type. Subsequently, for each mobile device 112, e.g., for each phone model type, an intensity information may be clustered or sorted (denoted with reference number 204). Further, for each intensity information and each mobile device 112, e.g., for each intensity information and each smartphone, a color information may be clustered or sorted (denoted with reference number 206). Specifically, the clustered intensity information and color information may be suited for revealing ambient lighting and image recording information specific for the respective mobile device 112 (denoted with reference number 208). As an example, an ambient lighting and image recording black box for each smartphone may be revealed respectively.

Further, the clustered data may be subjected to a branching point 210 deciding, based on a quantity of the clustered data, between a first branch 212 and a second branch 214. Specifically, the amount of data for each cluster may be checked, deciding on whether the amount of data is "enough" ("y") or "not enough" ("n").

Specifically, artificial neural networks (ANN) may be used, such as for image analysis. In principle, an optical and/or colormetric test strip algorithm may be based on using an ANN. However, in order to train an image-based neural net like, e.g., any type of convolutional neural net (CNN), enough data, such as more than a predetermined threshold amount of data, should be available, for example data covering a plurality of circumstances, such as blood glucose values for a plurality of influencing factors, e.g., independently and combined. Thus, the second branch 214 indicating the amount of data to be "not enough" may lead to aborting the method (denoted with reference number 216).

If the amount of data is considered to be "enough," e.g., deciding on the first branch 212, the CNN may be trained according to the clustered data (denoted with reference number 218). Subsequently, CNN quality may be validated with separate test data (denoted with reference number 220). Subsequently, a performance of the neural net, such as the CNN, may be subjected to another condition query or branching point 222, wherein the performance of the neural net, e.g., of the CNN, may be validated. A passed validation may lead to step 198 of setting the clearance information flag to a state indicating a sufficient level of confidence. In case the validation is not passed, again, the method may be aborted 216.

As an example, available reference card measurement data from any reference card based app release may be used to partially train an image based neural net. In particular, reference card data may be reused for training smartphone specific aspects as well as scene specific aspects.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 system
112 mobile device
114 camera
116 determination method
118 controlling method
120 evaluation device
122 processor
124 optical test strip
126 test field
128 color reference card
130 server device
132 cloud-based evaluation device
134 step i)
136 step ii)
138 step iii)
140 branching point
142 first branch
144 second branch
146 step iv)
148 step I)
150 step a.
152 step b.
154 step c.
156 step d.
158 external factors
160 handling aspect
162 sample variable
164 external variable
165 RGB data of image
166 image acquisition
168 image processing
170 camera setting variable
172 optical variable
174 image scene variables
176 tone mapping
178 color transformation matrix
180 demosaicing
182 capturing at least one image of at least a part of an optical test strip having a test field by using the camera
184 determining at least one analyte concentration value from color formation of the test field
186 branching point—check of cloud access
188 first branch indicating "cloud access"
190 second branch indicating "no cloud access"
192 branching point
194 first branch indicating "sufficient" level of confidence
196 second branch indicating "insufficient" level of confidence
198 setting the clearance information flag to a state indicating a sufficient level of confidence
200 storing measurement details
202 clustering collected data according to mobile device
204 clustering intensity information
206 clustering color information
208 revealing ambient lighting and image recording information
210 branching point—check amount of data
212 first branch indicating "enough"
214 second branch indicating "not enough"
216 aborting the method
218 train convolutional neural net according to the clustered data
220 validate neural net quality with separate test data
222 branching point—validation

What is claimed is:

1. A method of determining a concentration of an analyte in a body fluid with a mobile device having a camera, the method comprising:

evaluating a plurality of analytical measurements and thereby determining a correlation wherein the correlation is configured for transforming color formation of a test field into an analyte concentration without requiring the use of a color reference card;

using the camera to capture an image of at least a part of an optical test strip having a test field;

determining an analyte concentration value from color formation of the test field of the optical test strip;

providing, in the mobile device, the correlation for transforming color formation of the test field into the analyte concentration;

providing, in the mobile device, an item of clearance information indicating a level of confidence for the correlation; and when the item of clearance information indicates a sufficient level of confidence for the correlation, the mobile device providing an indication to a user that the capturing of the image does not require using a color reference card.

2. The method according to claim 1, wherein the item of clearance information comprises a clearance information flag having a state indicating an insufficient level of confidence and a state indicating a sufficient level of confidence.

3. The method according to claim 1, further comprising: when the item of clearance information indicates an insufficient level of confidence for the correlation, the mobile device indicating to a user that the capturing of the image requires capturing of an image of a color reference card.

4. The method according to claim 1, wherein the correlation for transforming color formation of the test field into the analyte concentration comprises transforming an item of color information derived from the image into the analyte concentration.

5. A method of controlling analytical measurements using a mobile device having a camera, the method comprising:
I) a data collection process comprising:
(a) carrying out a plurality of analytical measurements, wherein the analytical measurements at least partly comprise capturing images of at least a part of an optical test strip having a test field by using the camera and further comprise capturing images of a color reference card;
(b) evaluating the plurality of analytical measurements and thereby determining a correlation configured for transforming color formation of the test field into an analyte concentration value without requiring using the color reference card;
© determining a level of confidence for the correlation determined in step (b);
(d) setting an item of clearance information indicating the level of confidence for the correlation; and
II) determining the concentration of an analyte in a body fluid with a process comprising:
using the camera to capture an image of at least a part of an optical test strip having a test field;
determining the analyte concentration value from color formation of the test field;
providing, in the mobile device, the correlation for transforming color formation of the test field into the analyte concentration value;
providing, in the mobile device, the item of clearance information indicating a level of confidence for the correlation; and
when the item of clearance information indicates a sufficient level of confidence for the correlation, the mobile device providing an indication to a user that the capturing of the image does not require using a color reference card.

6. The method according to claim 5, wherein step (b) comprises evaluating the images captured in step (a) and thereby identifying similarities in at least some of the images.

7. The method according to claim 6, wherein the identifying of similarities in at least some of the images comprises identifying similarities in groups of the images.

8. The method according to claim 5, wherein step (b) comprises using an artificial neural network.

9. The method according to claim 5, wherein step (d) comprises comparing the level of confidence with a predetermined threshold value, and, based on the comparison, setting the item of clearance information to a value indicating an insufficient level of confidence for measurements without using the color reference card or a sufficient level of confidence for measurements without using the color reference card, respectively.

10. A system for controlling analytical measurements, the system comprising: a mobile device having a camera; and wherein the system is configured for carrying out the method according to claim 5.

11. The system according to claim 10, further comprising an evaluation device configured for performing at least steps (b), (c) and (d).

12. The system according to claim 11, wherein the evaluation device is separate from the mobile device and is configured for communicating with the mobile device, wherein the evaluation device is configured for transmitting the item of clearance information to the mobile device.

13. A non-transitory computer readable medium having stored thereon computer-executable instructions for the mobile device having the camera to perform the method of claim 1.

14. A mobile device having a camera, the mobile device being configured for performing the method of determining a concentration of an analyte in a body fluid according to claim 1.

* * * * *

UNITED STATES PATENT AND TRADEMARK OFFICE
CERTIFICATE OF CORRECTION

PATENT NO. : 12,287,327 B2
APPLICATION NO. : 17/752597
DATED : April 29, 2025
INVENTOR(S) : Benhur Aysin et al.

Page 1 of 1

It is certified that error appears in the above-identified patent and that said Letters Patent is hereby corrected as shown below:

In the Claims

Column 31, Line 29, Claim 5, "©" should be --(c)--.

Signed and Sealed this
Tenth Day of June, 2025

Coke Morgan Stewart
*Acting Director of the United States Patent and Trademark Office*